United States Patent [19]

Biggs

[11] 4,397,634

[45] Aug. 9, 1983

[54] SURGICAL PINS AND METHOD

[76] Inventor: Anthony J. Biggs, 9 Pulman La., Godalming, Surrey, England

[21] Appl. No.: 144,928

[22] Filed: Apr. 29, 1980

[30] Foreign Application Priority Data

Jun. 20, 1979 [GB] United Kingdom ............... 7921416

[51] Int. Cl.³ .............................................. A61C 5/04
[52] U.S. Cl. ................................................. 433/225
[58] Field of Search .............. 433/225; 148/16.7, 136; 266/262, 263, 250

[56] References Cited

U.S. PATENT DOCUMENTS

| | | | |
|---|---|---|---|
| 2,199,326 | 4/1940 | Unckel | 148/16.7 |
| 2,452,931 | 11/1948 | Jacob | 266/262 |
| 2,910,772 | 11/1959 | Chechik | 433/225 |
| 3,123,469 | 3/1964 | Tanczyn | 148/136 |
| 3,395,455 | 8/1968 | Overby et al. | 433/225 |
| 3,466,748 | 9/1969 | Christensen | 433/189 |
| 3,579,831 | 5/1971 | Stevens et al. | 433/201 |
| 3,606,615 | 9/1971 | Rudiger et al. | 433/201 |
| 3,675,328 | 7/1972 | Weissman | 433/225 |
| 3,675,329 | 7/1972 | Weissman | 433/225 |
| 3,718,324 | 2/1973 | Westeren et al. | 266/250 |
| 3,861,043 | 1/1975 | Lieb et al. | 433/225 |
| 3,896,547 | 7/1975 | Kulwiec | 433/207 |

FOREIGN PATENT DOCUMENTS 905714 7/1972 Canada ............................... 433/225

Primary Examiner—John J. Wilson
Attorney, Agent, or Firm—Murray & Whisenhunt

[57] ABSTRACT

A self-tapping surgical pin which is capable of plastic deformation at ambient temperature is formed of vacuum-annealed orthopaedic stainless steel.

7 Claims, 7 Drawing Figures

SURGICAL PINS AND METHOD

This invention relates to surgical pins and more particularly to surgical pins for use as rentention aids in dental and orthopaedic surgery.

In dentistry, superstructures are generally built on understructures constituted by broken or undermined teeth by providing in the understructure a number of protruding pins about which the superstructure is formed. The pins were originally constituted by lengths of wire introduced into a mass of unset dental cement located in an oversize bore drilled into the dentine.

More recently, the practice which has developed has involved drilling a number of undersize bores into the dentine understructure and inserting into the bores to extend therefrom oversize screw-threaded dental pins. Such a procedure is described in U.S. Pat. Nos. 3,434,209 and 3,675,328. Generally, each of the pins employed is self-tapping, the self-tapping action of the pin being accomplished by using a sharp edge thread on the pin which forces the dentine out of the way as the pin is threadedly advanced therein. Thus the pins are thread-forming as against thread-cutting (see British Standard 4174:1972). With thread-cutting pins, their rotation serves to cut out of the way material bordering the undersize bore into which they are introduced. An example of a thread cutting pin is that disclosed in U.S. Pat. No. 3,861,043.

It is usual to introduce pins into the bores either by use of a power tool or manually. In either case, it is generally the practice to fit the pin in the chuck of either a power tool or a hand tool as the case may be. In preferred practice, however, which enables the use of a power tool to be avoided and which avoids the risk of pins falling out of worn and thus loose chucks, according to what is described and claimed in my British patent specification No. 1,528,245, the pin forms part of a disposable surgical hand wrench. The wrench is integral and comprises an elongate body which may be considered to comprise four parts, namely a portion intermediate the ends which is of reduced thickness, a thread-forming self-tapping second portion which serves as the surgical pin and which is comprised by a length of the elongate body between the portion of reduced thickness and one end of the elongate body, a third portion of the elongate body at the other end thereof which is of cylindrical form and has a diameter greater than that of any part of the elongate body and which is sized for rotation between finger and thumb and a fourth portion which separates the first and third bodies. The first portion of reduced thickness is such that when said one end reaches the bottom of an undersized bore pre-drilled into hard tissue such as dentine, the second portion is unable to rotate further and the application to the third portion of like force to that previously applied for rotation of the wrench results in the second portion shearing from the remainder of the wrench at the first portion. The dental pin of U.S. Pat. No. 3,861,043 also forms part of a hand wrench to be operated between finger and thumb, but as previously indicated, this pin is thread-cutting rather than thread-forming and moreover the hand wrench is not of integral construction.

In order to enhance the fixing of a superstructure on an understructure using surgical pins thus provided in hard tissue, it is often the practice to bend the dental pin once it is firmly in place in the hard tissue. This bending is generally carried out using small pliers and may result in a portion of the pin being set at about 45° with respect to the line of the remainder of the pin. Any attempt to increase the bending of the pin and thereby achieve a formation approaching that of a hook is generally unsuccessful because of the brittleness of the material employed. The dental pin simply breaks as further bending stress is placed thereon.

A preferred material for use in the production of dental pins is orthopaedic stainless steel. This material is of particular value because it is readily workable to produce hand wrenches of the aforesaid type while enabling a weakened area of reduced thickness as aforesaid to be produced which is able to withstand rupture during normal insertion of the surgical pin part of the wrench into a bore and yet shears as soon as the pin reaches the base of the bore. One form of orthopaedic steel which meets this requirement is the alloy En58J according to B.S. 1970-1955 (also designated as 316S16 according to British Standard 1970-part 4). Such alloys are non-magnetic as is generally required of stainless steels employed in surgery and essentially consists of from 8 to 12% nickel, from 17 to 20% chromium, from 2.50 to 3.50% molybdenum, silicon in a minimum amount of 0.20% and carbon, manganese, sulphur and phosphorus in maximum amounts of 0.12, 2.00, 0.045 and 0.45% respectively, the remainder being iron and unavoidable impurities. The alloy may optionally contain small amounts of titanium and niobium. Moreover, particularly when operating in the dental field, the steel alloy may additionally contain 0.2% selenium to increase the free machining properties. When the pin forms part of a dental wrench according to our British patent specification No. 1,528,245, the thread of the portion of the wrench forming a thread-forming pin may be produced by cutting or by rolling. Such alloys enable particularly accurate processing to be achieved. A roll cut is however approximately 20% stronger than a cut thread without affecting the shearing properties of the pin.

It has now been found that surgical pins which meet the aforesaid requirements of surgical pins, and in particular surgical pins for use in dentistry while additionally being sufficiently plastic to allow substantially unlimited capability for bending when the pins are emplaced in pre-drilled bores are obtained if the metal from which the pin is made is subjected to vacuum annealing. These pins are still capable of accurate processing, especially by machining, while maintaining characteristics which, particularly when the pins form part of surgical wrenches, allow rotation of the dental pin into a pre-drilled bore to take place reliably until the bottom of the bore is reached at which time further rotation of the wrench results in shearing of the second portion forming the dental pin from the remainder of the wrench.

The vacuum annealing may be applied to surgical pins in general, but, in particular to dental pins. The pins may be pins employed in the chucks of power and hand tools but preferably pins which form part of hand wrenches to be operated between finger and thumb, in particular the hand wrench of my British Patent Specification No. 1,528,245. Any non toxic stainless steel may be employed in forming the pins. However, it is prefered to employ orthorpaedic or surgical stainless steel of which the aforementioned alloy En58J is particularly preferred because it does not undergo discoloration during vacuum annealing. In general, discoloration of surgical pins according to this invention, especially when they are to be employed for dental purposes is to be avoided since there is a considerable risk that the discolouration will be visible through the relatively translucent dental enamel possessed by many people. In contrast, the almost white colour of undiscoloured surgical steel cannot be seen in this manner.

The vacuum annealing process may be carried out before machining of the metal from which the pins are to be formed is effected or after the pins have been formed. In the vacuum annealing process, the pins are placed in a furnace which is then evacuated and the pins are then heated to elevated temperature under inert atmospheric conditions. Temperature control will be effected so as to ensure that the metal from which the pins are made or are to be made achieves a certain plasticity which will allow it to be bent freely. The atmospheric conditions in the furnace during the annealing will be such as to ensure that discolouration of the metal does not occur. Although the process is termed "vacuum" annealing, in addition to maintaining a vacuum in the furnace during the heating procedure, it is also possible for an inert gas to be passed over the pins during the heating provided that the gas is not one which will react with a metal of the steel being annealed to cause discolouration. Thus, a noble gas or, in particular nitrogen may be employed for this purpose.

The preferred form of industrial vacuum furnace to employ when carrying out the vacuum annealing is an Ispen furnace. In preferred procedure, the annealing is carried out as follows. Firstly a small quantity of metal elements to be vacuum annealed is placed in a furnace. The furnace is then evacuated to create a controlled atmosphere. The furnace is then heated to from 1025° to 1075° C., preferably about 1050° C. and the maximum temperature reached is held for from 15 to 45 minutes, preferably for half an hour. After this time, an inert gas, preferably nitrogen is introduced into the furnace which is cooled down to room temperature. By operating in this manner discolouration of metal is avoided particularly well so that pins of metal annealed in this way will not cause any visual problems when disposed under some of the lighter dental materials used in the mouth or, of course, relatively translucent dental enamel. This procedure causes very little distortion of metal which would also be a considerable problem if finished, already threaded pins, were being subjected to vacuum annealing.

The vacuum annealing process to which the steel of pins embodying this invention is subjected, while technically a hardening process, gives to the surgical pins produced extreme flexibility. After insertion into a pre-drilled bore in hard tissue, the pins will be capable of bending by more than 90° from their original line of insertion. This will enable much greater retention of superstructure forming material to be achieved thereby enabling a much more stable dental restoration to be obtained. Moreover, because of the flexibility of the pin it will be possible to contour it into the natural line of the completed restoration.

For a better understanding of the invention and to show how the same may be carried into effect, reference will now be made, by way of example only, to the accompanying drawings, wherein.

In the drawings, like reference numerals represent like parts in each Figure.

Figure 1:
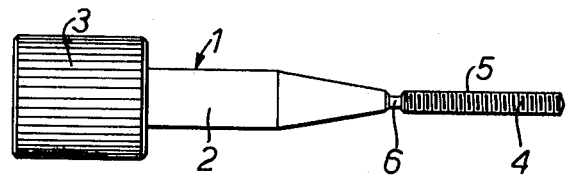
FIG. 1 is a plan view of a dental wrench according to my British patent specification No. 1,528,245.

Referring firstly to FIG. 1, there is shown a dental wrench 1 formed by cutting from a single rod of orthopaedic stainless steel which is preferably an orthopaedic stainless steel alloy of the type referred to earlier herein, and comprising a cylindrical portion 2 adjoining a ribbed handling portion 3 of greater diameter and joined to a portion 4 of smaller diameter and carrying screw-threading 5 by means of a neck portion 6 of reduced thickness and providing an area of predetermined weakness.

Figure 2:
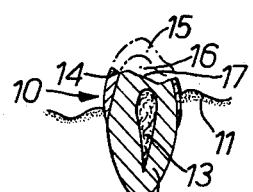
FIG. 2 is a section through a tooth from which decayed matter has been removed to form an understructure ready to receive a superstructure.

Referring next to FIG. 2, there is shown a tooth 10 in the soft tissue 11 of the human gum. The body 12 of the tooth 10 is formed of dentine and encloses a pulp channel 13. The dentine projecting from the soft tissue is covered by a layer 14 of enamel. In order to prepare the tooth for building a superstructure thereon, a portion 15 of the enamel and a portion 16 of the dentine are excavated to remove decayed and undermined understructure and form the excavated surface 17 free of decay.

Figure 3:
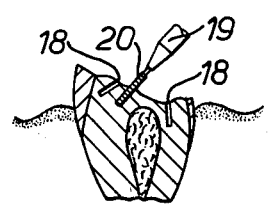
FIG. 3 is a similar view to that shown in FIG. 2 but to an enlarged scale showing the drilling of bores in the dentine understructure.

To provide a superstructure on the excavated surface 17, a plurality of bores 18 are drilled into the dentine from the surface 17 using a drill 19 as shown in FIG. 3. The bit 20 of the drill may possess a diameter of for example 0.5 cm. The number of channels 18 needed in a particular understructure will vary with the area of excavated surface 17 and portion of dentine 16 and enamel 15 that must be replaced by superstructure. In certain cases, a single bore may be sufficient.

Figure 4:
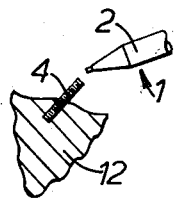
FIG. 4 is a similar view to FIG. 3 which on a further enlarged scale indicates the manner in which a dental pin is introduced into a bore in the dentine understructure.

Turning next to FIG. 4, a dental pin 4 is provided in the dentine 12. For this purpose, the wrench 1 shown in FIG. 1 is brought up to a bore 18 (FIG. 3) and is manually turned to introduce the screw-threaded pin to the bore. In the illustrated example, the pin will have a diameter of about 0.0064 cm. When the pin has reached the bottom of the bore 18, further twisting of the wrench will result in the portion 2 being sheared from the pin as a result of rupture at the neck portion 6. The portion of the wrench remaining in the operators hand is then discarded and a fresh wrench selected for emplacement of a pin in any further bore.

Figure 5:
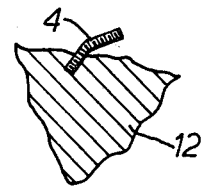
FIG. 5 is a similar view to FIG. 4 showing a dental pin in the configuration which it has hitherto been possible to bend it into.

When a dental pin has been inserted in thread-forming self-tapping manner in each bore 18, one or more of the pins may then be subjected to bending to enhance the attachment of a superstructure to the substructure. Bending has generally been carried out using a pair of pliers to achieve a shape of pin 4 as shown in FIG. 5.

The superstructure is then built on the exposed excavated surface utilising the support capacity of the dentine and the benefit of the projecting pins for retaining the superstructure in place.

Figure 6:
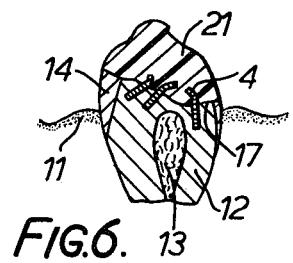
FIG. 6 is a similar view to FIG. 3 showing a superstructure secured to a dentine understructure by means of dental pins provided by means of a wrench and subsequently bent over as shown in FIG. 5.

Thus referring to FIG. 6, a superstructure 21 can be seen to be formed over the excavated surface 17 of the tooth.

Figure 7:
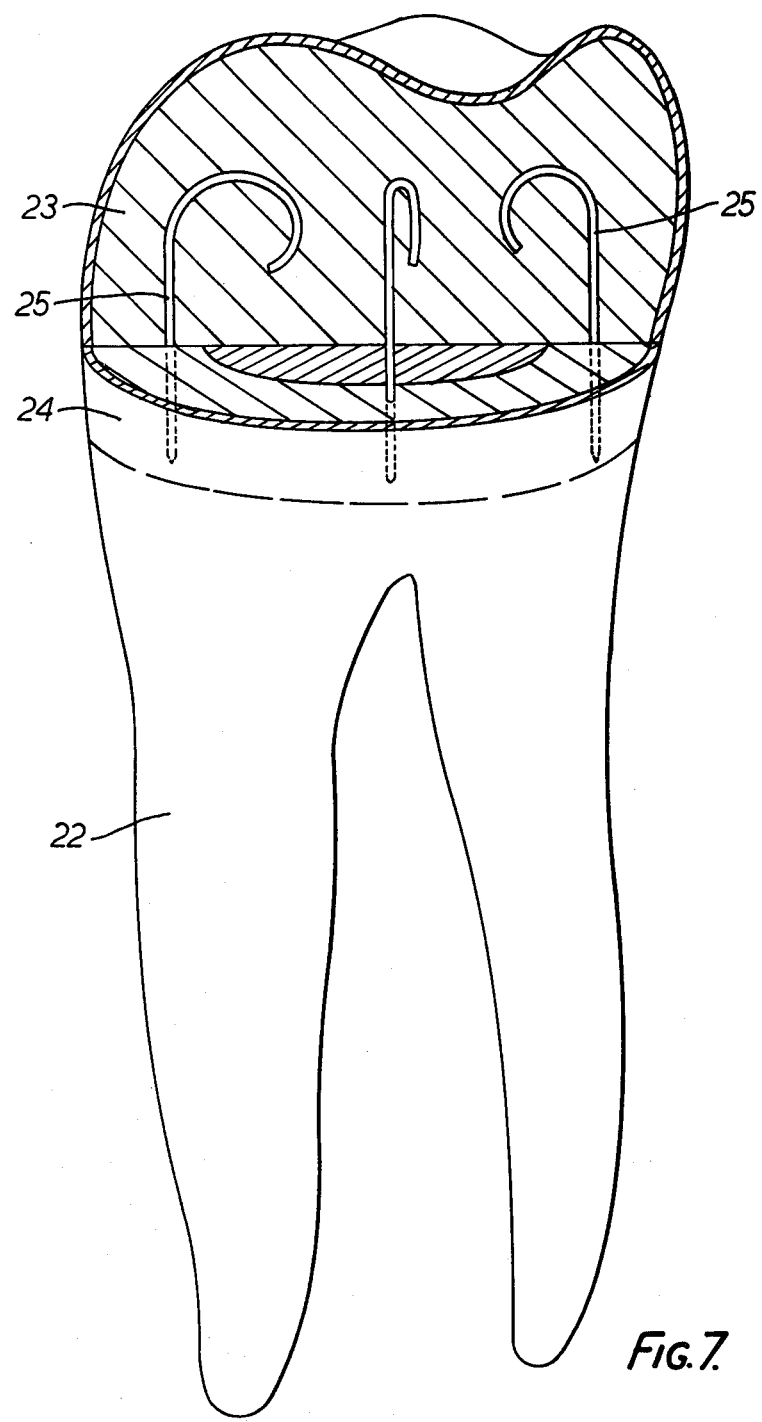
FIG. 7 is an elevation, with part cut away, of a tooth showing a superstructure secured to a dentine understructure by means of dental pins according to the present invention.

Referring finally to FIG. 7, there is shown a molar 22 having a crown 23 applied as a superstructure over a dentine substructure shown at 24. To assist the fixing of the crown, a plurality of dental pins 25 is provided in pre-drilled bores in the dentine 24. Instead of being given a simple bend as shown in FIG. 5, the pins because they had been subjected to vacuum annealing thereby rendering them plastic have been formed at their exposed ends into hooks which considerably enhance the retention of the crown. This plastic character in no way prevents the insertion of the pins into the pre-drilled bores and the required shearing from the handling part of the hand wrench of which they previously formed part.

I claim:

1. A self-tapping dental pin which is formed of orthopaedic stainless steel which has been vacuum-annealed to an extent sufficient to render it plastic in the cold and of uniform light color, which pin is comprised by a disposable hand wrench and is intended for emplacement in an undersized bore drilled into hard tissue, the wrench comprising an elongate body, a first portion of which intermediate the ends thereof is of reduced thickness, a second portion of which is between the first portion and one end and is a thread-forming self-tapping portion constituted by said pin, and a third portion of which at the other end is of cylindrical form having a diameter greater than that of any other part of the elongate body, said third portion being sized for rotation between finger and thumb, said elongated body being integrally formed and said first portion of reduced thickness having shearing means such that when said one end reaches the bottom of the undersized bore, said second portion is unable to rotate further and the application to said third portion of like force to that previously applied for rotation results in said second portion shearing at said first portion from the third portion, and wherein at least the said second portion which is formed of vacuum annealed orthopaedic stainless steel is bendable by more than 90° after shearing from said third portion.

2. A pin as claimed in claim 1 which is formed of an orthopaedic stainless steel which essentially consists of from 8 to 12% nickel, from 17 to 20% chromium, from 2.50 to 3.50% molybdenum, silicon in a minimum amount of 0.20%, carbon, manganese, sulphur and phosphorus in maximum amounts of 0.12, and selenium being optionally present in an amount of 0.2%, the remainder being iron and unavoidable impurities.

3. A pin as claimed in claim 1, which is formed of an orthopaedic stainless steel which essentially consists of from 8 to 12% nickel, from 17 to 20% chromium, from 2.50 to 3.50% molybdenum, silicon in a minimum amount of 0.20%, carbon, manganese, sulphur and phosphorus in maximum amounts of 0.12, 2.00, 0.045 and 0.045% respectively, selenium optionally present in an amount of 0.2% and titanium and/or niobium optionally being present in minor amount, the remainder being iron and unavoidable impurities.

4. In restorative dentistry, a method of providing an anchor for restorative material to be provided at a damaged portion of a tooth, which comprises the steps of drilling an undersized bore into dentine exposed by damage to the tooth, introducing into the tooth to occupy it a self-tapping dental pin which is formed of orthopaedic stainless steel which has been vacuum-annealed to an extent sufficient to render it plastic in the cold and of uniform light color, the pin being introduced in such manner that it retains a straight configuration, and subjecting the pin while it is in screw-threaded engagement with the dentine to plastic deformation to give it a curved form over at least part of its length by bending it by more than 90° at at least one position whereby its ability to act as an anchor for restorative material is enhanced, wherein the pin is incorporated in a disposable hand wrench which comprises an elongate body, a first portion of which intermediate the ends thereof is of reduced thickness, a straight thread-forming self-tapping second portion of which serving as said pin is comprised by a length of elongate body between the portion of reduced thickness and one end of the elongate body and a third portion of which elongate body at the other end thereof is of cylindrical form having a diameter greater than that of any other part of the elongate body, said third portion being sized for rotation between finger and thumb and being separated from said first portion by a fourth portion of elongate body, which wrench is integrally formed, said second portion retaining its straight form during introduction into the bore and said first portion of reduced thickness having shearing means such that when said one end reaches the bottom of the undersized bore, said second portion is unable to rotate further and the application to said third portion of like force to that previously applied for rotation of the wrench results in fracture and said second portion shears from the remainder of the wrench at said first portion.

5. A method according to claim 4, wherein the pin is formed of an orthopaedic stainless steel which essentially consists of from 8 to 12% nickel, from 17 to 20% chromium, from 2.50 to 3.50% molybdenum, silicon in a minimum amount of 0.20%, carbon, manganese, sulphur and phosphorous in maximum amounts of 0.12, 2.00, 0.045 and 0.45% respectively, and selenium optionally present in an amount of 0.2% with titanium and/or niobium optionally being present in minor amount, the remainder being iron and unavoidable impurities.

6. A method according to claim 4, wherein the pin is formed of an orthopaedic stainless steel which essentially consists of from 8 to 12% nickel, from 17 to 20% chromium, from 2.50 to 3.50% molybdenum, silicon in a minimum amount of 0.20%, carbon, manganese, sulphur and phosphorus in maximum amounts of 0.12, and selenium being optionally present in an amount of 0.2%, the remainder being iron and unavoidable impurities.

7. A method according to claim 4, wherein the wrench has been subjected to vacuum annealing after formation thereof.

* * * * *